US011865312B2

(12) United States Patent
Ploch et al.

(10) Patent No.: US 11,865,312 B2
(45) Date of Patent: Jan. 9, 2024

(54) RFID DOSE TRACKING MECHANISM FOR INJECTION DEVICES

(71) Applicant: SANOFI, Paris (FR)

(72) Inventors: Markus Ploch, Frankfurt (DE); Maurice Toporek, Frankfurt am Main (DE)

(73) Assignee: Sanofi, Paris (FR)

( * ) Notice: Subject to any disclaimer, the term of this patent is extended or adjusted under 35 U.S.C. 154(b) by 700 days.

(21) Appl. No.: 16/954,351

(22) PCT Filed: Dec. 18, 2018

(86) PCT No.: PCT/EP2018/085394
§ 371 (c)(1),
(2) Date: Jun. 16, 2020

(87) PCT Pub. No.: WO2019/121615
PCT Pub. Date: Jun. 27, 2019

(65) Prior Publication Data
US 2021/0085879 A1 Mar. 25, 2021

(30) Foreign Application Priority Data
Dec. 21, 2017 (EP) ..................................... 17306865

(51) Int. Cl.
A61M 5/315 (2006.01)

(52) U.S. Cl.
CPC ...... A61M 5/3155 (2013.01); A61M 5/31525 (2013.01); A61M 2205/3553 (2013.01); A61M 2205/60 (2013.01)

(58) Field of Classification Search
CPC .......... A61M 5/31511; A61M 5/31566; A61M 2005/3125; A61M 2205/3389;
(Continued)

(56) References Cited
U.S. PATENT DOCUMENTS 7,935,088 B2   5/2011  Veasey et al.
2001/0034506 A1  10/2001  Hirschman et al.
(Continued)

FOREIGN PATENT DOCUMENTS

CA        2689017      11/2002
CN      101268336       9/2008
(Continued)

OTHER PUBLICATIONS

PCT International Preliminary Report on Patentability in International Appln. No. PCT/EP2018/085394, dated Jun. 23, 2020, 8 pages.

(Continued)

Primary Examiner — Bradley J Osinski
(74) Attorney, Agent, or Firm — Fish & Richardson P.C.

(57) ABSTRACT

Described is a dose tracking mechanism for a drug delivery device, including a moveable component configured to move with respect to a housing during operation of the drug delivery device and an RFID device with an electric circuit having a resonance frequency. The electric circuit includes an antenna configured to transmit a wireless RFID signal at the resonance frequency and an electrical component operatively coupled to the moveable component and configured to modify the resonance frequency based on a position of the moveable component, such that the resonance frequency of the electric circuit is an indication of the position of the moveable component. In some instances, the position of the moveable component indicates a dose set or dispensed from the drug delivery device.

19 Claims, 9 Drawing Sheets

(58) Field of Classification Search
CPC .. A61M 2205/3592; A61M 2205/3561; A61M 5/31525
See application file for complete search history.

(56) References Cited

U.S. PATENT DOCUMENTS

| | | |
|---|---|---|
| 2004/0171983 A1 | 9/2004 | Sparks et al. |
| 2005/0015055 A1* | 1/2005 | Yang ............... A61B 5/150694 604/199 |
| 2009/0043253 A1 | 2/2009 | Podaima |
| 2009/0318876 A1 | 12/2009 | Hansen et al. |
| 2010/0292685 A1 | 11/2010 | Katoh et al. |
| 2011/0152825 A1 | 6/2011 | Marggi |
| 2011/0264033 A1 | 10/2011 | Jensen et al. |
| 2013/0310756 A1 | 11/2013 | Whalley et al. |
| 2014/0214001 A1 | 7/2014 | Mortazavi |
| 2014/0221914 A1 | 8/2014 | Calasso |
| 2015/0018771 A1 | 1/2015 | Schenker et al. |
| 2016/0259913 A1 | 9/2016 | Yu et al. |
| 2017/0147918 A1 | 5/2017 | Karani et al. |
| 2017/0316157 A1 | 11/2017 | Riedel et al. |
| 2021/0104309 A1 | 4/2021 | Felber et al. |

FOREIGN PATENT DOCUMENTS

| | | |
|---|---|---|
| CN | 103961765 | 8/2014 |
| CN | 104321096 | 1/2015 |
| CN | 104661696 | 5/2015 |
| CN | 105999481 | 10/2016 |
| EP | 2764881 | 8/2014 |
| EP | 3244947 | 10/2021 |
| JP | 2009-542388 | 12/2009 |
| WO | WO 2007/039148 | 4/2007 |
| WO | WO 2009/024562 | 2/2009 |
| WO | WO 2014/033195 | 3/2014 |
| WO | WO 2016/113348 | 7/2016 |
| WO | WO 2017/016959 | 2/2017 |
| WO | WO 2017/021227 | 2/2017 |

OTHER PUBLICATIONS

PCT International Search Report and Written Opinion in International Appln. No. PCT/EP2018/085394, dated Mar. 7, 2019, 11 pages.

* cited by examiner

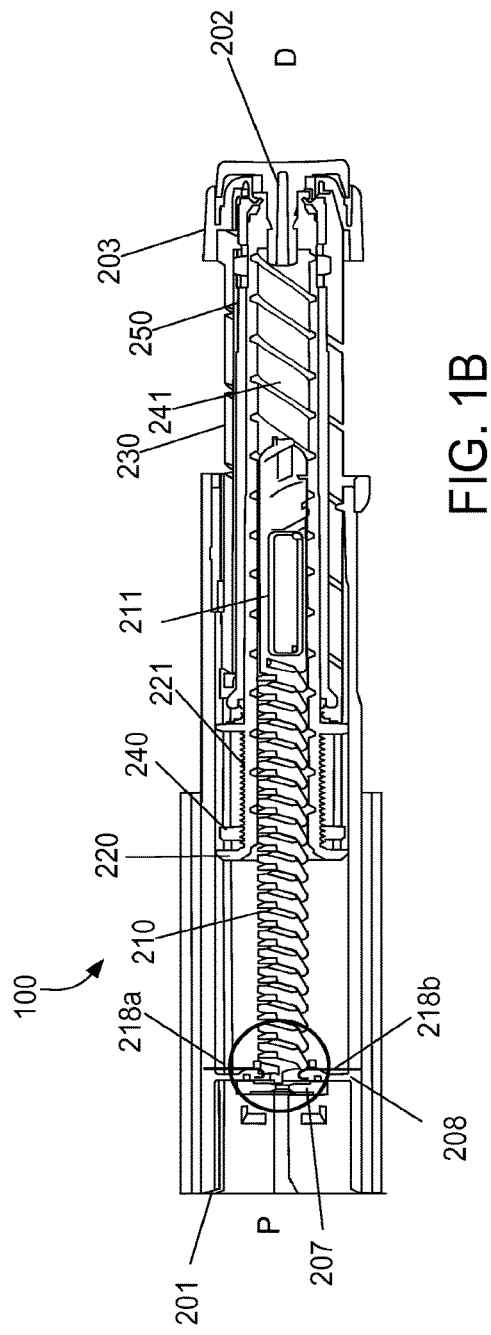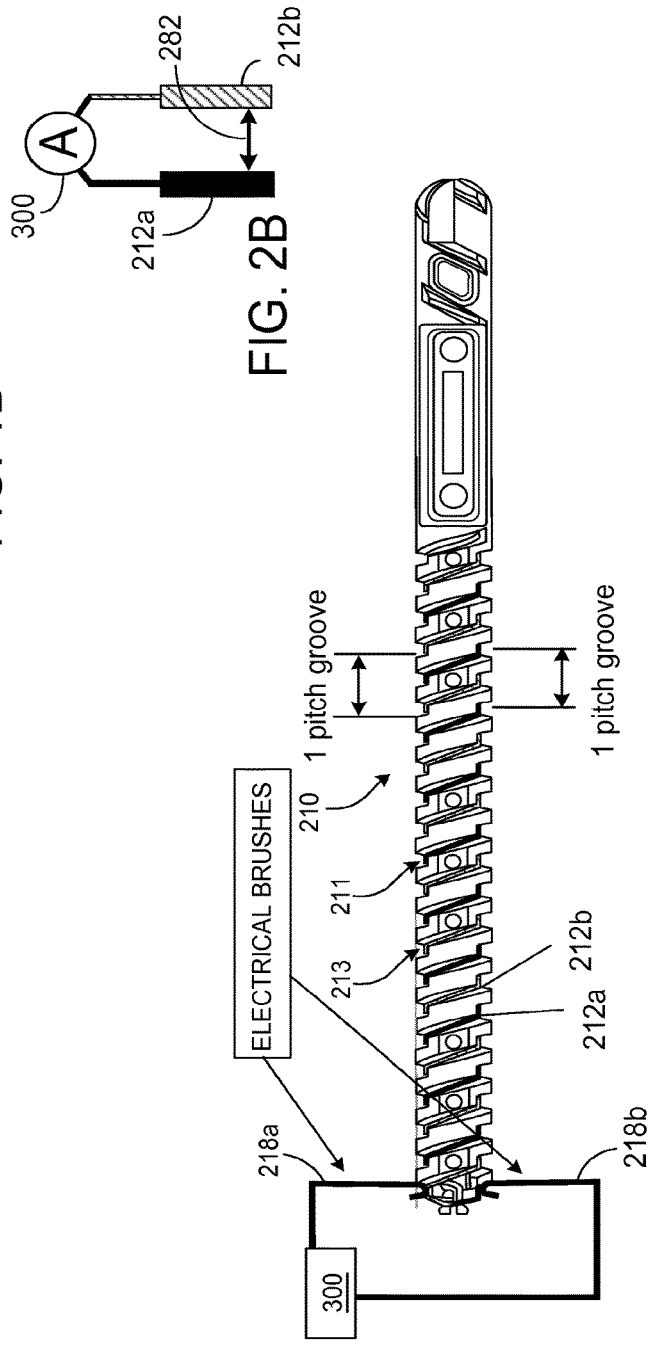

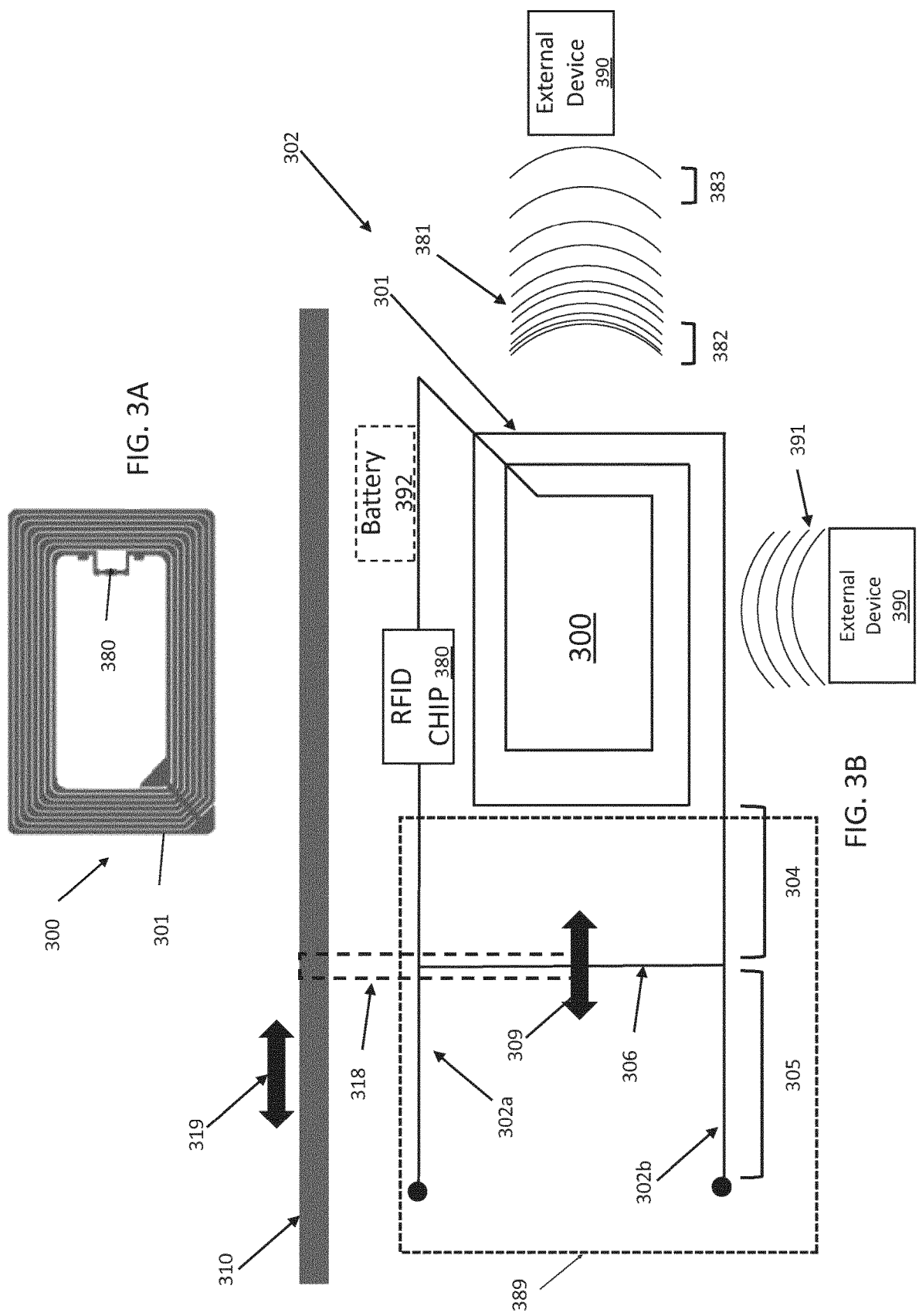

RFID DOSE TRACKING MECHANISM FOR INJECTION DEVICES

CROSS REFERENCE TO RELATED APPLICATIONS

The present application is the national stage entry of International Patent Application No. PCT/EP2018/085394, filed on Dec. 18, 2018, and claims priority to Application No. EP 17306865.1, filed on Dec. 21, 2017, the disclosures of which are incorporated herein by reference.

TECHNICAL FIELD

This description relates to a dose tracking mechanism for modulating the resonance frequency of an RFID signal to track the amount of a dose delivered from a drug delivery device.

BACKGROUND

A variety of diseases can be treated by injection of a medicament. Such injections can be performed using drug delivery devices, which can be applied either by medical personnel or by patients themselves. As an example, type-1 and type-2 diabetes can be treated by patients themselves by injection of drug doses, for example once or several times per day. For instance, a pre-filled disposable drug pen or autoinjector can be used as a drug delivery device. Alternatively, a re-usable pen or autoinjector may be used. A re-usable pen or autoinjector allows replacement of an empty medicament cartridge (or any other kind of medicament container) by a new one. Either type of pen or autoinjector may come with a set of one-way needles that are replaced before each use. The medicament dose may vary individually, therefore a user (e.g., a patient or health care professional) may select the amount of medicament required (e.g. dial a dose) by operating a dose setting mechanism of the drug delivery device prior to use.

Medical devices can include electronics capable of changing their resonance frequency in order to analyze various components of the medical device. For instance, EP 2764881A1 discloses a transponder circuit which is contactless coupled to moveable fluid-tight membranes. Displacement of the fluid-tight membranes in EP 2764881A1 can cause a change in the resonant frequency of the transponder circuit, helping a user to monitor occlusion or other atypical conditions of the medical device.

SUMMARY

This disclosure relates to drug delivery devices having RFID electronics capable of changing their resonance frequency in order to track a set or delivered dose of a medicament from the drug delivery device. This principle is based on using an RFID chip, which typically includes a memory and an antenna formed by an electric circuit. In operation, when the RFID chip is in the reach of a reader device such as a smart phone with an RFID reader, the antenna receives a signal from the smart phone and sends a wireless response signal according to the information encoded in the memory of the chip.

In a representative example, the electric circuit of the antenna is in a closed circuit (e.g., completing the circuit and enabling the antenna to transmit the response signal) with a variable electronics device, such as a variable resistor or capacitor, where the configuration of the variable electronics device is operatively coupled with the movements of one or more components of the drug delivery device responsible for a dose setting or dispensing operation of the drug delivery device. In this manner, when a position of a component of the drug delivery device (e.g., part of a dose setting mechanism or a dose dispensing mechanism) changes during a dose setting operation or a dose dispensing operation dose, a corresponding change in the configuration of the variable electronics device in an RFID device's electric circuit is made. As a result, the resonance frequency of the RFID's device changes and this change indicates the change in position of the component. The change in position is therefore an indication of the dose set during the dose setting operation or a dose dispensed during the dose dispensing operation.

For example, if 10 units of a medicament is delivered from a drug delivery device with a corresponding movement of a dose dispensing mechanism, the variable electronics component is adjusted by an amount corresponding to the 10 units, and this, in turn, causes a change in the resonance frequency of the RFID's device that indicates 10 units of change of the dose dispensing mechanism. As an illustrative example, an RFID device has a default resonance frequency of 13.00 MHz and a variable electronics device in the circuit of the RFID device is coupled to a dose dispensing device such that changing in position of the dose dispensing mechanism changes the resonance frequency by +0.1 MHz for every unit of dose dispensed by the dose dispensing device by changing a property of the electric circuit of the RFID device (e.g., resistance, capacitance, or inductance). Therefore, after dispending 10 units of dose (and before the dose dispensing device's position is reset), the resonance frequency of the RFID device is changed to 14.00 MHz. This new resonance frequency, as read by an external device, is usable as an indication that 10 units of dose were dispensed from the drug delivery device.

Aspects of this system can be implemented in a drug delivery device in a number of ways. In one example, a plunger rod (e.g., a leadscrew) has two conductive wires running down a helical track, and the plunger rod is advanced though a bearing nut during a dose dispensing operation. The two conductive wires are embedded in the helical track and joined atone end of the plunger rod. The bearing nut has two metal brushes contacting the two conductive wires and the RFID device has an electric circuit connected across the two metal brushes. Therefore, the length of wiring of the RFID circuit (e.g., the RFID chip plus a portion of conductive wiring of the plunger rod defined by the position of the metal brushes) is changed by the position of the plunger rod with respect to the bearing nut. Thus, as the plunger rod is advanced though the bearing nut during a dose dispensing operation, a resonance frequency of the RFID signal is modified as the resistance of the electric circuit is changed, because the resonance frequency is a function of the total resistance in the electric circuit. In another example, a variable resistor of an RFID device is connected to the plunger rod such that rotation of the plunger rod rotates a component of the variable resistor and changes the resistance, which results in a change in the resonance frequency of the RFID device.

In addition, a medicament and/or dose information can be transmitted with the encoded information of the RFID chip. In some instances, this may be only a unique tag serial number, or may be product-related information such as a stock number, lot or batch number, production date, or other specific information. Because RFID chips can have individual serial numbers, aspects of the present RFID tracking mechanism can discriminate among several tags that might be within the range of the RFID reader (i.e., an external device) and read several tags simultaneously. In this manner, it can be ensured that only the correct device is interrogated and the respective response is captured by the RFID reader.

Certain aspects of the present disclosure result in several advantages beyond the ability to easily track a set and/or dispensed dose from a drug delivery device. For example, a drug delivery device often includes a serial, stock, batch number, or production date in addition to information regarding the medicament, such as expiration, drug name, drug type, and concentration. Because an RFID chip is able to store specific data stored in a local memory, including any of the aforementioned information, and transmit this data in the RFID signal itself. This data can also be centrally tracked by the manufacturer to assist in recalls, track and analyze patient behavior, and monitor product usage. The use of a passive RFID chip has the advantage of being simple, reliable, and cost-effective. Additionally, with existing drug delivery devices, there are only minor modifications required to the dose delivery or setting mechanism to integrate the RFID chip, due to the small size and thickness of typical RFID chips.

An example embodiment of the present disclosure is a dose tracking mechanism for use in a drug delivery device. The dose tracking mechanism includes a housing, a moveable component configured to move with respect to the housing during operation of the drug delivery device, and an RFID device. The RFID device includes an electric circuit having a resonance frequency, where the electric circuit includes an antenna configured to transmit a wireless RFID signal at the resonance frequency, and an electrical component operatively coupled to the moveable component and configured to modify the resonance frequency based on a position of the moveable component, such that the resonance frequency of the electric circuit is an indication of the position of the moveable component.

In some instances, the moveable component is configured to move between a plurality of possible positions with respect to the housing, and wherein each of the plurality of positions of the moveable component causes a different resonance frequency of the electric circuit of the RFID device, such that each different resonance frequency is an indication of a different position of the moveable component.

In some instances, the electrical component is configured to vary an electrical property of the electrical component as a function of the position of the moveable component, wherein the resonance frequency of the RFID device is configured to be a function of the electrical property varied by the electrical component, and wherein the electrical property is one or more of the following: capacitance, inductance, or resistance.

In some instances, the doses tracking mechanism includes a dose setting mechanism having the moveable component, and wherein the position of the moveable component corresponds to a dose of medicament to be delivered by the drug delivery device as set by the dose setting mechanism, and wherein the resonance frequency is an indication of the dose of medicament set by the dose setting mechanism.

In some instances, the doses tracking mechanism includes a dose dispensing mechanism having the moveable component, and wherein the position of the moveable component corresponds to a dose of medicament dispensed from the drug delivery device by the dose dispensing mechanism, and wherein the resonance frequency is an indication of the dose of medicament dispensed from the drug delivery device.

In some instances, the doses tracking mechanism includes a dose memory mechanism having the moveable component, and wherein the position of the moveable component corresponds to a total dose of medicament remaining in the drug delivery device, and wherein the resonance frequency is an indication of the total dose of medicament remaining in the drug delivery device.

In some instances, the electrical component is a variable electronic resistor comprising a conductive electrode disposed in a track along the moveable component.

In some instances, the electrical component is a variable resistor comprising a conductor disposed in a track along the moveable component. In some instances, the track is a first track comprising a first conductor, and the variable resistor comprises a second conductor disposed in a second track along the moveable component.

In some instances the electrical component is a variable resistor including a first component having a track spanning at least a portion of a length of the first component, and first and second conductors along the track, a second component moveable with respect to the first component along the track, the second component contacting the first and second conductors, and an electrical contact between the first and second conductors having resistance proportional to a position of the second component along the length of the first component. The electric circuit of the RFID device is connected to the variable resistor across the electrical contact, the moveable component of the drug delivery device comprises the first component or the second component, and the position of the second component with respect to the first component is changed during a dose setting operation or a dose dispending operation of the drug delivery device.

In some instances, the RFID device is carried by the second component.

In some instances, the track comprises a single thread and the first and second conductors are disposed on opposite sides of a crest of the single thread, and wherein the second component is in threaded engagement with the first component In some instances, the track comprises a first thread and a second thread, and the first conductor is disposed along the first thread, and the second conductor is disposed along the second thread, and wherein the second component is in threaded engagement with the first component.

In some instances, the first component is a threaded sleeve configured to move helically with respect to the housing during a dose setting operation, and wherein the second component is a thread insert carried by the housing, wherein the moveable component is the threaded sleeve and the resonance frequency corresponds to a dose set during the dose setting operation.

In some instances, the first component is a leadscrew configured to move helically with respect to the housing during a dose dispensing operation of the drug delivery device to translate a stopper into a cartridge of the drug delivery device, wherein the second component comprises a bearing nut carried by the housing, and wherein the moveable component is the leadscrew and the resonance frequency corresponds to the position of the stopper in the cartridge which corresponds to a dose dispensed from the cartridge during the dose dispensing operation.

In some instances, the first component is a threaded plunger rod, and the second component is a last dose nut configured to thread along the drive sleeve during the dose setting operation, and wherein the moveable component is the last does nut and the resonance frequency corresponds to a dose remaining in the drug delivery device.

In some instances, the wireless signal comprises identification information related to the drug delivery device or a medicament contained therein.

In some instances, the RFID device is a passive RFID device configured to transmit the wireless RFID signal in response to a wireless reader signal received by the electric circuit of the passive RFID device.

In some instances, the RFID device includes a power source, and wherein the RFID device is an active RFID device configured to receive power from the power source and to transmit the wireless RFID signal using the received power.

In some instances, the active RFID device is configured to transmit the wireless signal in response to an activation of a trigger mechanism of the drug delivery device, the trigger mechanism initiating a dose dispensing operation.

In some instances, the RFID device is configured to transmit a first wireless RFID signal before the dose dispensing operation and a second wireless RFID signal after the dose dispensing operation. In some instances, the resonance frequency of the first RFID signal corresponds to a dose set by the dose setting mechanism or a dose remaining in the drug delivery device before the dose dispensing operation, and the resonance frequency of the second wireless signal corresponds to the dose dispensed during the dose dispensing operation or the total dose remaining in the drug delivery device after the dose dispensing operation.

DESCRIPTION OF FIGURES

FIG. 1B is a cross sectional view of a portion of the drug delivery device of FIG. 1A.

FIGS. 2A and 2B are illustrations of a dose dispensing mechanism with a conductive track forming a variable electronic device of a dose tracking mechanism.

FIG. 3A is an illustration of an RFID circuit.

FIGS. 3B and 3C are illustrations of a dose tracking mechanism having the RFID circuit.

DETAILED DESCRIPTION

Figure 1A:
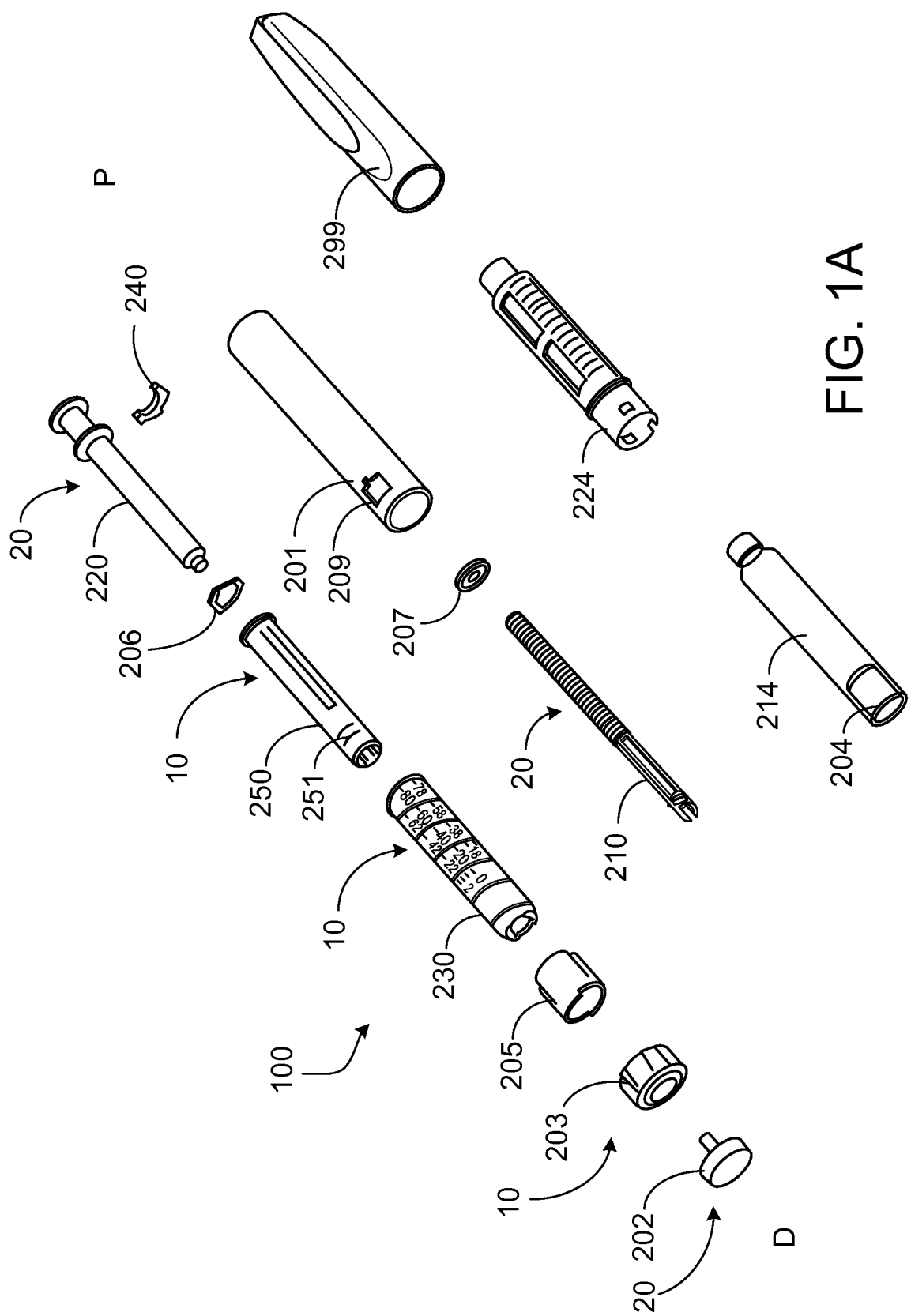
FIG. 1A is an exploded view of a drug delivery device.

Cartridge-based injection and medical syringe systems can include integrated electronics that enable detection of a dose set by the user or a measurement of the medicament delivered by the device (e.g., a position sensor), along with some feature for presenting this information to the user. For example, a digital display arranged to display a dose or a wireless connection to transmit the dose data. However, the above examples typically require an internal source of power, either to run the sensor(s) or the wireless transmission. Certain aspects of the present disclosure provide a drug delivery device with a dose tracking mechanism generating a wireless RFID signal that encodes one or more of a dose set and a dose delivered by the drug delivery device without the need for an internal power source. Certain aspects also relate to a dose tracking mechanism that generates the wireless RFID signal using an active (e.g., battery powered) RFID transmitter.

Certain aspects of the present disclosure measure the amount of medicament dispensed from a container, e.g. a cartridge, and use this information to determine the amount of medicament that a patient has received during an injection event. The principle is based on using an RFID chip that includes a memory and an antenna with a resonance frequency able to be modified by the movement of components of the drug delivery device, as detailed below. The RFID chip is placed inside a drug delivery device (e.g., a pen-shaped injection device) and is in wireless transmitting range a reader device such as a smart phone. The RFID device's antenna receives a signal from the reader device and sends a response according to the information encoded in the memory of the chip. The response signal is "tuned" (e.g., frequency modulated) according to the position of an element inside the delivery device (e.g., a lost dose nut or a dose dispensing mechanism).

The RFID signal may include information related to, for example a unique tag serial number, or may be product-related information such as a stock number, lot or batch number, production date, or other specific information such as drug compound. Since tags have individual serial numbers, the RFID system design can discriminate among several tags that might be within the range of the RFID reader and read them simultaneously. In this way, only the right device is interrogated and the respective response is captured by the reader.

In an example embodiment, an electrical property (e.g., resistance) of an RFID circuit varied depending on the position of the last dose nut of a drug delivery device. For example, the last dose nut includes an RFID device and the thread on which it travels comprises a galvanic/conductive track that has a certain resistance. The resistive value varies with the position of the last dose nut. Adding this resistance to the RFID circuitry would result in a slightly modified frequency. The value of the modified or detuned frequency can be determined by the RFID reader when receiving the signal. The amount of detune is proportional to the distance the last dose has traveled along the thread. As the frequency is varied with the position of the last dose nut, each position can be identified by a certain amount of detuned frequency. In some instances, the system is be calibrated during manufacturing, when the resistance of the track is known. In some instances, the frequency difference in relation to the initial frequency is taken as a measure and the difference is used to calculate an amount of medicament delivered or remaining.

In a typical usage scenario, a patient would launch an application on a reader, such as a smart phone, once it is time for an injection. Alternatively, a reminder function of the application could prompt the patient to start the injection. While the user is preparing for an injection, the reader device is close by the patient and queries the drug delivery device with a wireless signal that is received by the RFID device in the drug delivery device. In response, the RFID device transmits a response signal to the reader, including information about the position of last dose nut as encoded by the frequency of the RFID signal. The processor of the reader device can determine from the position information (a) the amount of medicament discharged and/or (b) the amount of medicament inside the pen/container. This can be done either based on a difference to the initial signal/amount or relative to the previous signal/amount.

$$Frequency_{initial} - Frequency \sim Amount_{initial} - Amount$$

OR $$Frequency_1 - Frequency_2 \sim Amount_1 - Amount_2$$

While the patient is performing the injection procedure, an application on the reader device is active in the sense that it queries the drug delivery device from time to time thus observing the movement of the last dose nut. Upon the user giving an "injection completed" signal (pressing on the display, voice signal "complete", or the like) the application is closed the RFID query is stopped. Alternatively, the application can be closed via a time out after a couple of minutes (e.g. 5 minutes after start). The application now has gathered information about time and medicament amount and can store this in a log.

In certain aspects, a variable electric component is provided as part of a dose tracking mechanism in a drug delivery device to modify the resonance frequency of an antenna of an RFID device (where the RFID device generally includes the RFID chip and antenna) in response to a movement of a dose tracking mechanism or a dose dispensing mechanism of the drug delivery device, such that the RFID device transmits an RFID signal at the modified resonance frequency, where the frequency is useable for calculating the dose set by the dose setting mechanism or the dose dispensed by the dose dispensing mechanism.

In a representative embodiment, an RFID device in a drug delivery device includes an electric circuit with a variable electronic device arranged to modify a property of the electric circuit (e.g., resistance, capacitance, inductance) in response to change in position of a component of the drug delivery device during a dose setting operation or a dose delivery operation, such that the variable electronic device changes the frequency of the RFID signal transmitted by the RFID device, and the frequency of the transmitted signal is an indication of the arrangement of the component of the drug delivery device. In some instances, the variable electronic device is operatively connected to or integrated with a component of a dose setting mechanism, such that the frequency of the RFID signal changes as a function of the dose set by the dose setting mechanism. In some instances, the variable electronic device is operatively connected to or integrated with a component of a dose dispensing mechanism, such that the frequency of the RFID signal changes as a function of the dose dispensed by the dose setting mechanism. In some instances, the variable electronic device is operatively connected to or integrated with a component of a dose memory mechanism, such that the frequency of the RFID signal changes as a function of the dose remaining in the drug delivery device. In operation, a received signal is transmitted from some external device, such as a smart phone or an RFID reader, and the RFID circuit of the drug delivery device transmits a response RFID signal at the resonance frequency. In this manner, for example, during a drug delivery operation, a dose dispensing mechanism moves an amount corresponding to the amount of medicament delivered. During this movement, the variable electronic device modifies a property of the RFID circuit such that the resonance frequency changes, and the change in the resonance frequency corresponds to the movement of the dose dispensing mechanism and, therefore, the resonance frequency also corresponds to the amount of the medicament delivered. The frequency of the RFID signal is then easily measured by an external device, and the amount of medicament delivered is determined based on a known relationship between the resonance frequency of the RFID signal and the dispensed amount of medicament. The known relationship could be, for example, that a given frequency corresponds to the dispensed amount. Alternatively, the relationship could be based on a comparison between a measuring of the frequency of the RFID signal prior to the dose dispensing operation, where a measured change in frequency corresponds to the dispensed amount.

While the above description includes a passive RFID system (i.e., no internal power source), passive RFID signals are often limited in this transmission distance. Alternatively, an active RFID chip could be used, where active RFID chips are generally understood to require a source of power beyond any received RF energy in order to generate the wireless response signal with more power. The design is similar in function compared to the above passive system, with the addition of a battery to boost the transmission power of the RFID signal. The power is only required to feed the system when in use. In some examples, an air-zinc battery is used to ensure that the drug delivery device is disposable, if necessary. In this instance, the air-zinc battery is arranged such that a protective latch is removed automatically when using the drug delivery device the first time at dial up. In some instances, the battery is located in the dose release button and the latch is fixed to a pen housing. Then the RFID device is ready, but, in some instances, does not initially transmit the RFID signal until a user activates the drug delivery device or until an external device queries the RFID device. In the active RFID system, similar to the passive system, an external device reads the frequency of the received RFID signal and computes the amount of medicament from the frequency, either by comparison to a baseline value, a change from a previous reading of the drug delivery device, or from by referencing a lookup table. In some instances, the actual data that is being sent from the RFID device in the wireless signal includes information on the medicament/device and this can be by the reader to interpret the data. For example, the external device can assign the measured frequencies to the "right" device and store it appropriately in a separate storage for this device/medicament.

FIG. 1A is an exploded view of a drug delivery device 100, which may be a disposable or reusable drug delivery device. The drug delivery device 100 includes a housing 201, covered by a replaceable cap 299, where the housing 201 contains a cartridge 214 and a cartridge housing 224 in which the cartridge 214 is disposed. A stopper 204 is disposed in the body of the cartridge 214 and can be advanced within the cartridge 214 during use to expel medicament from the cartridge 214. A needle assembly can be affixed to the cartridge housing 224 or the cartridge 114 to deliver the medicament. To drive the stopper 204 into the cartridge 214, the drug delivery device 100 includes a piston rod 210, a drive sleeve 220, and a trigger button 202 (e.g., a dose dispensing mechanism 20), which act together to drive a pressure plate 207 against the stopper 204 and into the cartridge 214. A medicament or drug dose to be ejected from the drug delivery device 100 is selected by turning a dosage knob 203, which is connected by a threaded insert 205 a dose dial sleeve 230, where rotation of the dose dial sleeve 230 by the dosage knob 203 causes the selected dose to be displayed in a dosage window 209 in the housing 201 and causes a clicker 250 to interact with the drive sleeve 220 via a spring clutch 206. Together, the dosage knob 203, dose dial sleeve 230, and clicker 250 are a dose setting mechanism 10. The dose dial sleeve 230 is arranged around a clicker 250, which includes a feedback mechanism 251 that generates a tactile or audible feedback with rotation of the dose dial sleeve 230. The clicker 250 is coupled to the drive sleeve 220 with a metal clutch spring 206, and a last dose nut 240 is provided on the drive sleeve 220. The last dose nut 240 advances with each dose dispensing operation to track the total medicament remaining in the cartridge 214. Finally, an injection button 202 is included, and depression injection button 202 activates a dose dispensing operation of the drug delivery device 100.

While the dose setting mechanism 10 is illustrated as the dosage knob 203, dose dial sleeve 230, and the clicker 250, as described above, one skilled in the art will appreciate that any number of different dose setting mechanisms are route in the art for the purposes of setting a dose of a drug delivery device and aspects of the present disclosure are compatible with other such dose setting mechanisms. Similarly, while the dose dispensing mechanism 20 is illustrated as a includes the piston rod 210, drive sleeve 220, trigger button 202, one skilled in the art will appreciate that any number of different dose dispensing mechanisms (e.g., drive mechanisms) are route in the art for the purposes of delivering or dispensing a dose of a drug delivery device and aspects of the present disclosure are compatible with other such dose dispensing mechanisms.

Continuing with the operation of the drug delivery device 100, turning the dosage knob 203 causes a mechanical click sound to provide acoustical feedback to a user by rotating the dose dial sleeve 230 with respect to the clicker 250. The numbers displayed in the dosage display 209 are printed on the dose dial sleeve 230 that is contained in the housing 201 and mechanically interacts with the drive sleeve 220 via the metal spring clutch 206 to interact with the cartridge 114. When the injection button 202 is pushed, the drug dose displayed in the display 209 will be ejected from the drug delivery device 100. During a dose setting operation, the drive sleeve is helically rotated with the dose dial sleeve 230 in the distal direction D. When the injection button 202 is pushed, the drive sleeve 220 is released and advanced proximally, which causes rotation of the piston rod 210. The rotation of the piston rod 210 drives the pressure plate 207 against the stopper 204 of the cartridge 214, which drives the stopper 204 into the cartridge 214 to expel the medicament from the cartridge 214. A more detailed description of a representative drug delivery device is described in U.S. Pat. No. 7,935,088 B2, issued May 3, 2011.

FIG. 1B is a cross sectional view of a portion of the drug delivery device 100 of FIG. 1A. FIG. 1B shows the drug delivery device 100 at the end of a dose setting operation and prior to a dose dispensing operation, where the dose dial sleeve 230 and the drive sleeve 220 have been helically rotated with respect to the housing 201 and a threaded end 211 of the piston rod 210 to set the dose. The last dose nut 240 is shown advanced along the drive sleeve 220 from an initial position to a position indicative of the dose remaining in the drug delivery device 100. Upon activation of the injection button 202, the drive sleeve 202 advances into the housing 201 and a bearing nut 208 induces rotation of the piston rod 210. The bearing nut 208 sits fixed inside the housing 201 and has a threaded engagement with a piston rod 210. As the piston rod rotates 210, the piston rod 210 is screwed forward (relative to the housing 201) because the bearing nut 208 cannot move. The rotation of the piston 210 drives the piston rod 210 and the pressure plate 207 proximally to drive the stopper 204 into the cartridge 214 (FIG. 1A).

FIGS. 2A and 2B are illustrations of a dose dispensing mechanism with conductive electrodes 212a, 212b in individual tracks 211, 213 forming a variable electronic resistor for use in a dose tracking mechanism. One aspects of the present disclose is based on modulating the resonance frequency of an RFID device as a function of the position of the plunger rod 210 (e.g., a leadscrew), which is a key component of the dose dispensing mechanism 20 of the drug delivery device 100 for use in expelling a dose of medicament. In dose dispensing a dose, the position of the plunger rod 210 changes with respect to the bearing nut 208 by rotating with respect to the bearing nut 208, and thus moving proximally along the axis of rotation. FIG. 2A shows a plunger rod 210 with embedded conductive elements 212a, 212b and stationary brushes 218a, 218b (e.g., conductive brushes, or electric brushes) forming a variable resistor that changes the resistance across the stationary brushes 218a, 218b as they move along the embedded conductive elements 212a, 212b. The plunger rod 210 thread has two parallel oriented grooves 211, 213 that include one of the embedded conductive elements 212a, 212b along the length of each the two parallel oriented grooves 211, 213 without interfering each other, except at one end of the grooves 211, 213 to create an open circuit across the brushes 218a, 218b.

In operation, the plunger rod 210 is driven proximally by the drive sleeve 220, and the grooves 211, 213 are threaded through the bearing nut 208, such that the proximal movement of the plunger rod 210 generates rotates the plunger rod 210 as it passes through the bearing nut 208. The stationary brushes 218a, 218b are disposed on the bearing nut 208 or otherwise fixed to the housing 201 and an RFID device 300 is connected across the brushes 218a, 218b. The resistance across the brushes 218a, 218b changes because of the change in total length of the conductive elements 212a, 212b between the brushes 218a, 218b. For example, as shown in FIG. 2A (and in FIG. 1), the stationary brushes 218a, 218b contact the conductive elements 212a, 212b close to the proximal end of the grooves 211, 213. The conductive elements 212a, 212b are in contact at either the proximal end or distal end of the grooves 211, 213, but not both. If at the distal end, the electric path from one brush 218a to the other brush 218b is down the entire length of the first groove 211 and back down the entire length of the second groove 213, a condition with represent the highest resistance configuration of the system. As the plunger rod 210 is driven though the bearing nut 208, the brushes 218a, 218b move along the grooves 211, 213, and the resistance between the brushes 218a, 218b decreases as the total length of the conductive elements 212a, 212b between the brushes 218a, 218b decreases. Alternatively, if the conductive elements 212a, 212b are in electrical contact at the proximal end, then the opposite configuration is true, and the resistance across the brushes 218a, 218b is at a minimum as shown, and increases at the plunger rod 210 is driven though the bearing nut 208. In some instances, each specific resistance represents one position of the plunger rod 210 and therefore the resistance corresponds to an amount of the dose expelled from the cartridge 214 by the plunger rod 210. In other instances, a change in the resistance corresponds to a change in position and is therefore proportional to the amount of medicament. Therefore, a relative change in resonance as compared to an initial resistance (e.g., before injection, or before a first use) corresponds to a measure for the medicament amount that has been expelled. As explained in more detail below with regard to FIGS. 3A-C, an RFID device 300 is connected across the brushes 218a, 218b such that the change in resistance causes a corresponding change in the resonance frequency of the RFID circuit.

FIG. 2B is a schematic of an alternative configuration, where the RFID device 300 is connected across the closed end of the conductive elements 212a, 212b, and a brush 282 completes the circuit across the conductive elements 212a, 212b at a variable location along the grooves 211, 213.

FIG. 3A is an illustration of a passive RFID device 300, which may be, e.g., an RFID circuit such as a printed RFID circuit. The RFID device 300 includes an RFID chip 380 and an antenna 301, where the antenna is coiled around the RFID device 300. In operation, the antenna 301 absorbs an incoming wireless reader signal from an external device and forms a weak magnetic field, which creates a current in the antenna to provide power to the RFID chip 380. The RFID chip 380 includes a memory, which stores, for example, information related to the drug delivery device 100 or a medicament contained therein. Upon power being provided to the RFID chip 380, the RFID generates a response signal in the antenna 301, which transmits the information from the RFID chip's 380 memory as a wireless signal. This wireless signal can be received by the external device that sent the reader signal, or by another device close by.

Figure 3C:
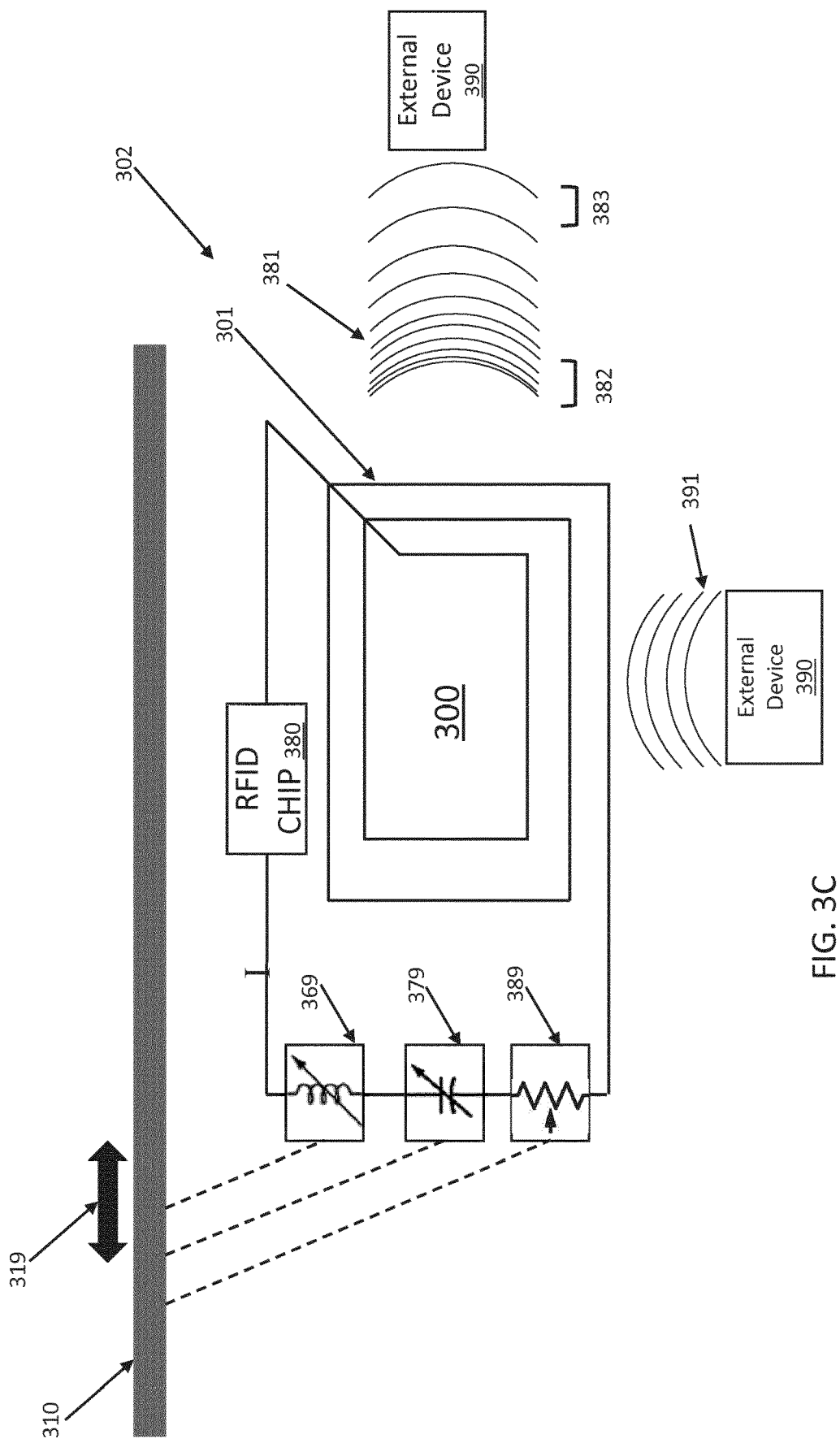

FIGS. 3B and 3C are illustrations of a dose tracking mechanism 302 having the RFID device 300. FIG. 3B is a schematic of the operation of a RFID dose tracking mechanism 302 in the drug delivery device 100 further including variable resistor 389 arranged to modify the resonance frequency of the antenna 301. The variable resistor 389 is operatively coupled to a moveable component 310 of the drug delivery device 100, such that movement of the component 310 (indicated by an arrow 319) results in a corresponding change in the resistance of the variable resistor 389, as detailed below. The RFID dose tracking mechanism 302 includes a RFID device 300 and an electric component 318 arranged to be moved by the moveable component 310 during operation of the drug delivery device 100. In some instances, the RFID dose tracking mechanism 302 includes a battery 392 configured to provide power to the RFID device 300 when the switch 370 is engaged, but as described above, the RFID dose tracking mechanism 302 can also be a passive RFID system, and FIG. 3B shows an external device 390 providing a wireless reader signal 391 to the antenna 301 of the RFID device 300 in order to generate power for the RFID chip 380. When powered (e.g., by the RF energy from the wireless reader signal 391), the antenna 301 of the RFID device 300 transmits a RFID signal 381 at a resonance frequency of the RFID device 300. The RFID signal 381 can then be received by the external device 390 and the resonance frequency of the RFID signal 381 can be measured. As detailed below, the variable resistor 389 changes the overall resistance of the RFID device 300, which enables the RFID antenna 301 to transmit the RFID signal 381 at a higher frequency 382 or a lower frequency 382, depending on the actuation of the variable resistor 389 during operation of the drug delivery device 100.

In operation, either passive or active, the moveable component 310 of the drug delivery device 100 is configured to operate the electric component 318 of the variable resistor 389 during a dose setting operation or a dose dispensing operation. For example, FIG. 3B shows that the variable resistor 389 includes two elongated conductive elements 302a, 302b, similar to the conductive elements 212a, 212b of FIG. 2A. Also similar to the brushes 218a, 218b of FIG. 2, in FIG. 3B a moveable electric connection 306 spans between the elongated conductive element 302a, 302b and puts them in electrical contact with each other. The elongated conductive elements 302a, 302b are connected at one end to the RFID device 300 and the location of the moveable electric connection 306 along the elongated conductive elements 302a, 302b determines the overall resistant of the RFID device 300 (e.g., by determining the overall portion of the elongated conductive element 302a, 302b that are in an electric circuit with the RFID device 300). The moveable electric connection 306 is connected to the moveable component 310 of the drug delivery device 100 via the electric component 318, which could be, for example, a nut having electric brushes (e.g., the moveable electric connection 306) in contact with elongated conductive elements 302a, 302b. As illustrated, the location of the moveable electric connection 306 along the elongated conductive elements 302a, 302b results in a first portion 304 of the elongated conductive elements 302a, 302b to be in the RFID device 300, and a second portion 305 of the elongated conductive elements 302a, 302b to be outside of the RFID circuit. Movement of the electric connection 306 along the elongated conductive elements 302a, 302b changes the length of the first and second portions 304, 305, and thereby varies the resistant of the variable resistor 389 of the RFID circuit.

One skilled in the art will appreciate that the configuration of FIG. 3B (with a stationary track and moveable electric connection 306) is the inverse of FIG. 2, where the conductive elements 212a, 212b move and the brushes 218a, 218b are stationary), but the variable resistant result of both configurations (FIG. 3B and FIG. 2) is the same.

In some instances, the moveable component 310 is part of a dose setting mechanism 10 such that moveable component 310 is moved during a dose setting operation, which results in a movement of the electric component 318 and, therefore, a change in the resistance of the variable resistor 389 corresponds to the movement of the dose setting mechanism and an amount of the dose set by the dose setting mechanism. In some instances, the moveable component 310 is part of a dose dispensing mechanism 20 such that moveable component 310 is moved during a dose dispending operation, which results in a movement of the electric component 318 and, therefore, a change in the resistance of the variable resistor 389 corresponds to the movement of the dose dispensing mechanism and an amount of the dose dispensed by the dose dispensing mechanism. In both cases, movement of the dose dispensing mechanism 20, dose setting mechanism 10, or some other mechanism of the drug delivery device (e.g., a dose memory mechanism) causes the electric component 318 to change the position of the electric connection 306 of the variable resistance 389, and thereby change the frequency of the transmitted RFID signal 381 such that the frequency of the RFID signal 381 is an indication of the position of the mechanism that is operatively coupled to the dose tracking mechanism 302. In additional, the movement of the component 310 that is actuated during operation of the drug delivery device 100 (e.g., the dose setting and/or the dispensing action) may involve rotational movement, as shown in FIG. 2B; alternatively, linear movement of the component 310 may also be used to operate the variable resistor 389, as shown in FIG. 3B.

The variable resistor 389 and the RFID antenna 301 are electrically connected via wires. The RFID device 300 could be placed on a housing component, preferably as a label (plastic, paper, adhesive RFID chip). Alternatively, the RFID device 300 could be located inside the housing 201, for example, at the inner surface of the injection button 202 or between injection button 202 and another inner component such as the dose dial sleeve 230.

Any number of variable electric components (of which a variable resistor 389 is one example) registers operation of some mechanism of the drug delivery device 100 (e.g., during a dial and/or dispense operation) and correlates this to modulate the RFID response signal 381. FIG. 3C illustrates different variable electric components 369, 379, 389 arranged in the RFID device 300. In some instances, the variable electric component is a variable inductor 369, and, in other instances, the variable electric component is a variable capacitor 379. One or more of the variable electric components 369, 379, 389 could be used in the dose tracking mechanism 302 to modulate the resonance frequency of the RFID device 300. The modulation is a change in the frequency of the RFID signal 381, which is an easily detectable property of the RFID signal as received by the external device 390. The variable electric components 369, 379, 389 can be arranged to modify the frequency of the response signal 381 in almost any matter that corresponds a movement of the mechanism of the drug delivery device 100 to which the variable electric components 369, 379, 389 is operatively coupled. In some instances, a variable electric component 369, 379, 389 is operatively coupled to a dose dispensing mechanism 210, and the frequency of the RFID signal 381 is proportional to the position of the plunger rod 210 after a dose dispensing operation. In this example, the frequency of the RFID signal 381 is an indication of the amount of dose dispensed from the drug delivery 210. In another example, the frequency is correlated to the dose that has been dialed or set. However, in this example, the drug delivery device includes a mechanism that can distinguish between up and down dialing and must "know" when a setting operation is ended (e.g., by sensing the start of the dose dispensing operation).

In an alternative dose tracking mechanism 302 configuration, a variable electric component 369, 379, 389 is arranged to be contacted or operated by contact by any adjacent components of the drug delivery device 100 that move relative to one another during operation (dose setting and/or dose dispensing). For example, movement between the dose dial knob 203 and housing 201, between the dose dial sleeve 230 and the window 209, or between the dose dial sleeve 230 and the housing 201.

Figure 4:
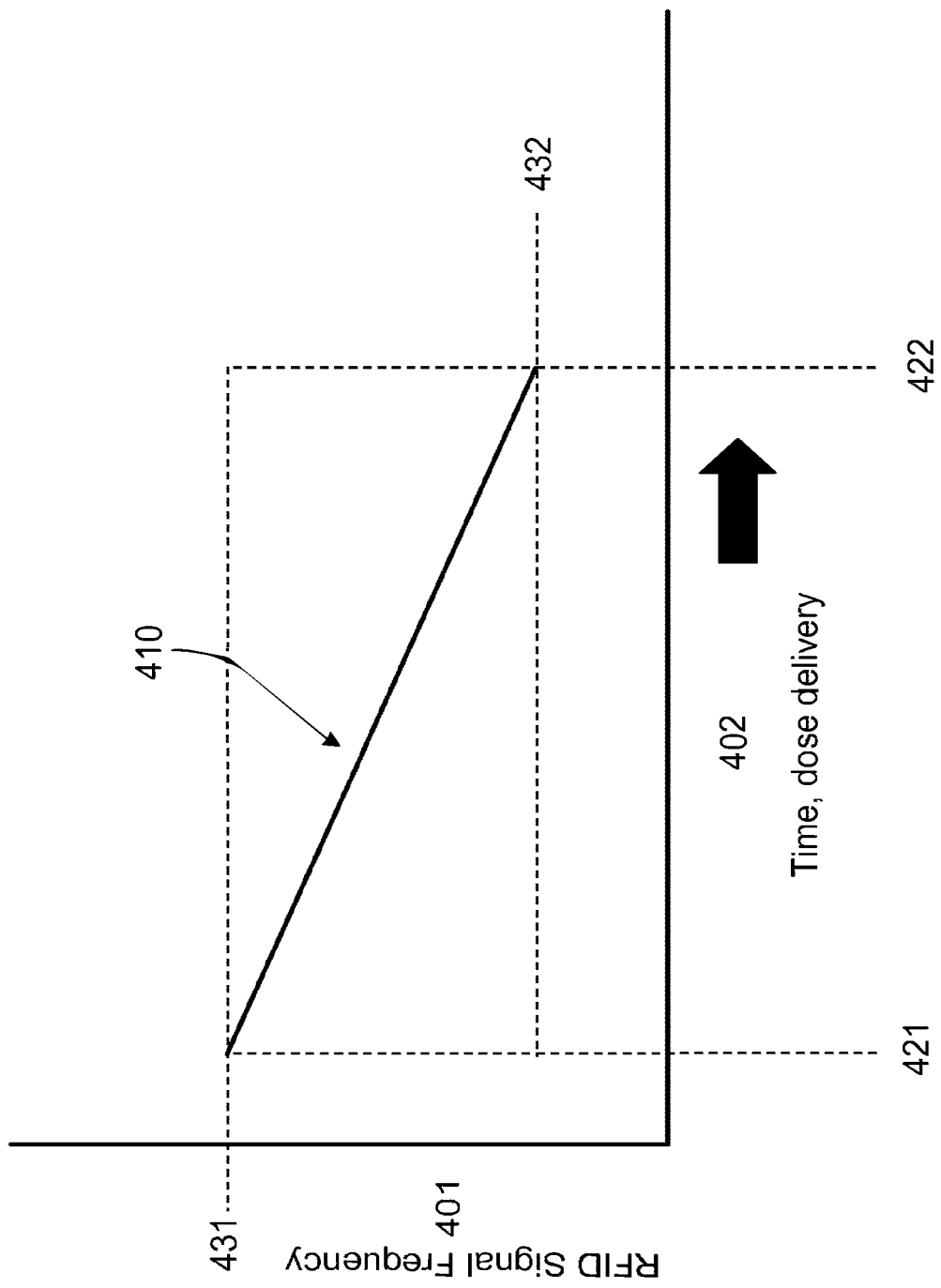
FIG. 4 is a graph of a change in the resonance frequency of an RFID device coupled to a dose dispensing mechanism during a dose dispensing operation.

FIG. 4 is a graph of resonance frequency 401 vs. times 402, and shows a change in the resonance frequency 410 of an RFID signal 381 transmitted from an RFID device 300 coupled to a dose dispensing mechanism 20 during a dose dispensing operation. Where RFID signal 381 also includes the information stored in the RFID chip 380. FIG. 4 illustrates how the frequency 410 of a transmitted RFID signal 381 changes during a dose dispensing operation, where a variable electric component 369, 379, 389 of an RFID device 300 is operatively coupled with an element of the dose dispensing mechanism 20. For example, a variable resistor 389 is arranged in the plunger rod 210 of a drug delivery device (e.g., FIG. 2B), such that the resistance of the variable resistor 389 increases as the plunger rod 210 is advanced during the dose dispensing operation from a first location at time 421, to a second location, at time 422. This change in position of the plunger rod 210 causes the variable resistor 389 to, for example, increase the total resistance of the RFID device 300, which results in a decrease in the frequency 410 of the RFID signal 381.

FIG. 4 illustrates how the frequency 410 of the RFID signal 381 decreases from a first frequency 431 at the first time 421 (e.g., before or at the start of the dose dispensing operation) to a second frequency 432 at the second time 422 (e.g., after or at the end of the dose dispensing operation). In some instances, the value of the second frequency 431 corresponds to the amount of the dose dispensed from the drug delivery device 100. In some instances, the value of the difference between the first frequency 431 and the second frequency corresponds to the amount of the dose dispensed from the drug delivery device 100. Generally, the external device 390 need not measure the entire history of the frequency 410 across the dose dispensing operation, but only measure the frequency at either the second time 422 or at the first and second times 421, 422, as detailed above. While FIG. 4 illustrates the change in frequency 410 with respect to time 402 as linear during a dose dispensing operation, other relationships are possible, if not more likely due to the typical non-constant movement of a plunger 210 during a dose dispensing operation. In many instances, the shape of the curve of the frequency 410 does not matter, as any measured value of the frequency can, some instances, correspond directly a position 319 of the plunger rod 210 (e.g., an amount of medicament dispensed), and there need not be a 1:1 correspondence such that an equal change in frequency 410 corresponds to an equal change in position 319. In still other instances, and in the case of an auto-injector where the force delivery of the dose dispensing mechanism is known, the external device 390 can measure the shape of the curve of the frequency 410 of the RFID signal 381 during the dose dispensing operation, where the shape can indicate other properties of the dose dispensing operation. Such as, for example, the rate of injection, which can be further used to calculate properties of the drug delivery device (e.g., restriction in the medicament flow, or a defect in the dose dispensing mechanism 20), properties of the medicament (e.g., viscosity and/or temperature), or properties of the patient's injection site.

Figure 5A:
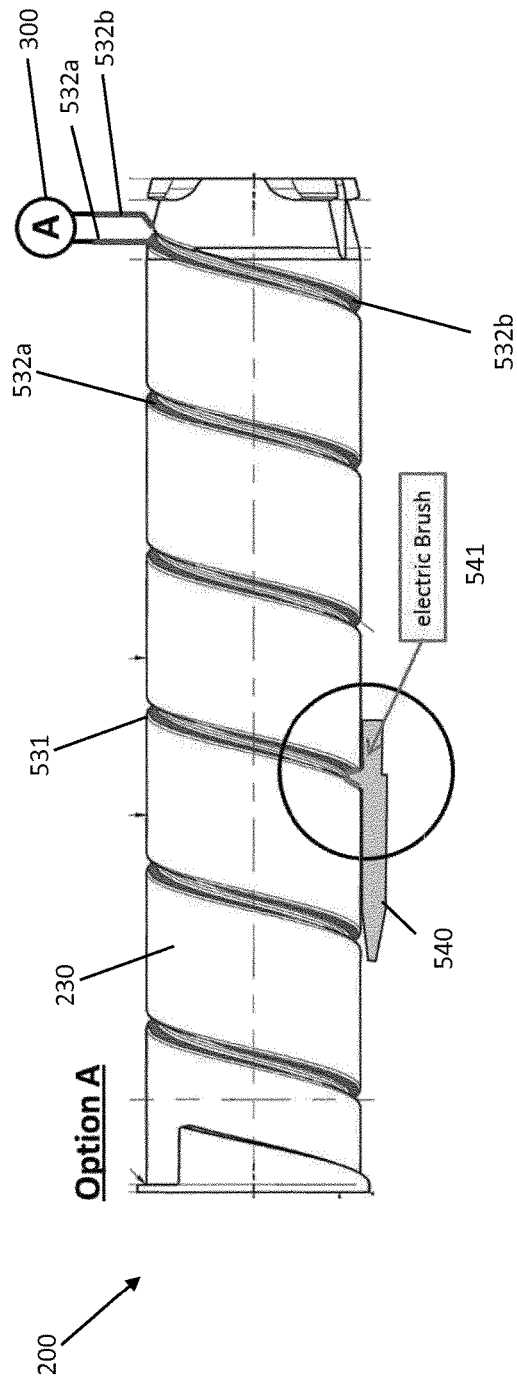
FIGS. 5A and 5B are illustrations of a dose setting mechanism with a conductive track forming a variable electronic device of a dose tracking mechanism.
Figure 5B:
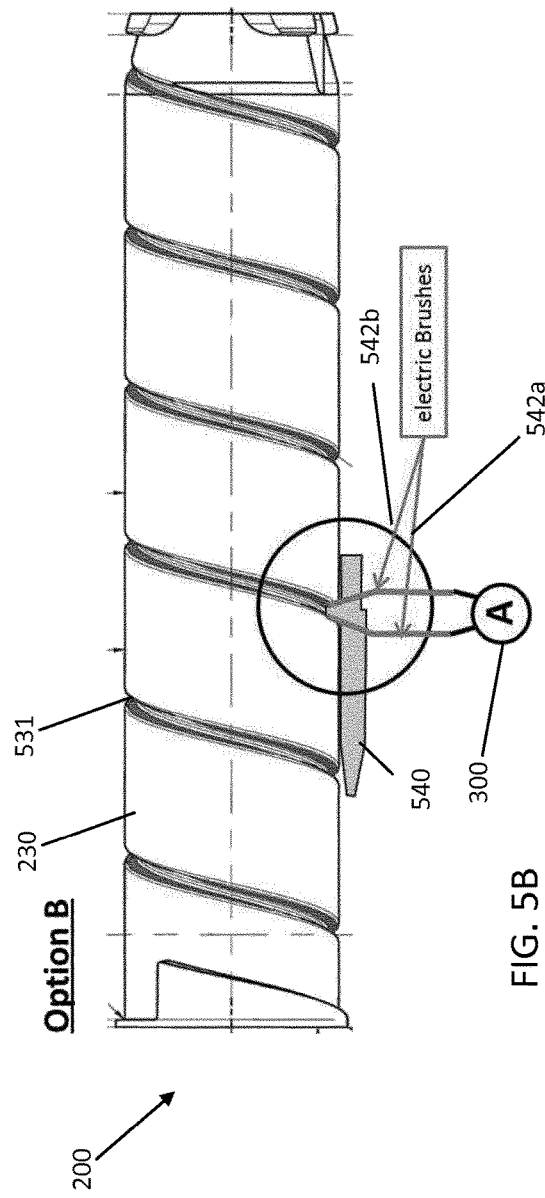

FIGS. 5A and 5B are illustrations of a dose setting mechanism with a conductive track forming a variable electronic device of a dose tracking mechanism. FIG. 5A shows a dose dial sleeve 230 (e.g., a number sleeve) with a single groove 531 arranged helically around the exterior of the dose dial sleeve 230. The track 531 includes first and second conductive elements 532a, 532b embedded along the grove 531 without interfering each other. The conductive elements 532a, 532b have a specific resistance, which behaves proportionally to the length.

In FIG. 5A, a thread insert 540 is shown integrated on the inside of the body 201 (FIG. 1). The thread insert 540 includes an electric brush 541 traveling along the groove 531 and in contact with both of the first and second conductive elements 532a, 532b to create a close end of a circuit. The other end of the circuit is completed with an RFID device 300 in contact across the first and second conductive elements 532a, 532b. Together, the first and second conductive elements 532a, 532b and the electric brush 541 define a variable resistor 389 in the RFID device 300, as described above. In operation, rotational movement of the dose dial sleeve 230 advances the or retracts the dose dial sleeve 230 from the housing 201, which also results in the thread insert 540 traveling along the groove 531 at a location corresponding to the position of the dose dial sleeve 320. When a user of the drug delivery device commences a dose setting operation to a dose, the position of the dose dial sleeve 320 changes through its thread by rotating, and thus moving proximally along the rotating axis with respect to the housing 201. This proximal move also translates the trigger button 202 disposed at the distal end of the dose dial sleeve 230. To dispense the pre-dialed dose, the trigger button 202 is pressed and the dose dial sleeve 230 is driven into the housing 201 by the user until the dose dial sleeve 230 returns to a zero dose (e.g., initial) position. In this manner, position of the brushes 541 in the groove 531 at the end of the dose setting operation indicate the amount of dose set by the user to be subsequently injected.

FIG. 5B shows an alternative configuration of the dose dial sleeve of FIG. 5A, where the RFID device 300 is carried by the thread insert 540. In FIG. 5B, the first and second conductive elements 532a, 532b are connected at one end of the groove 531 and first and second brushes 542a, 542b in the thread insert 540 individual contact the first and second conductive elements 532a, 532b and the RFID circuit is connected across the first and second brushes 542a, 542b In some instances, the thread insert 540 is an external component of drug delivery device 201 an the RFID circuit is a printed label on the exterior of the thread insert 540 and connected across the first and second brushes 542a, 542b, which are exposed to the exterior surface.

Figure 6:
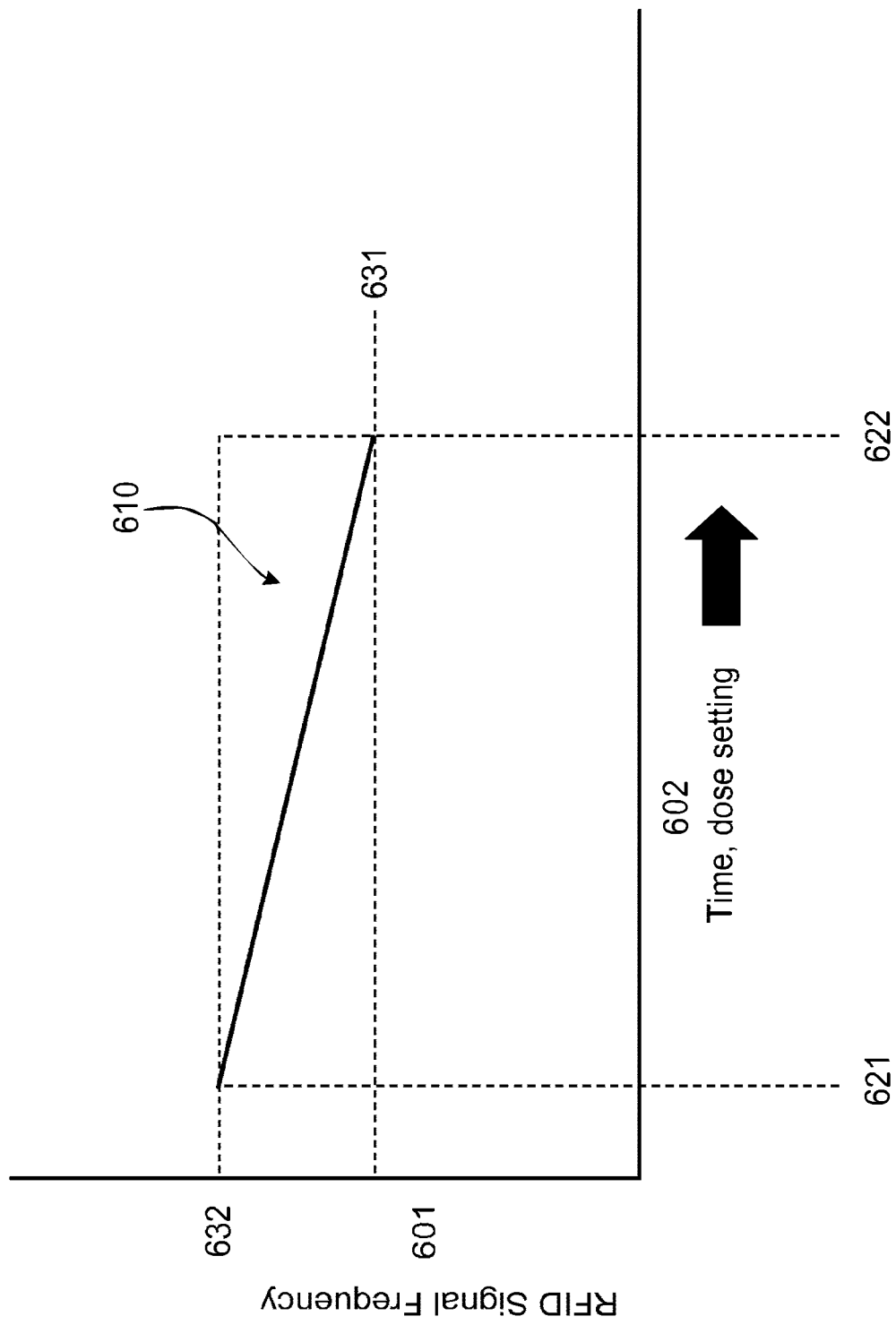
FIG. 6 is a graph of a change in the resonance frequency of an RFID device coupled to a dose setting mechanism of during a dose setting operation.

FIG. 6 is a graph of a change in the resonance frequency of an RFID device coupled to a dose setting mechanism of during a dose setting operation. FIG. 6 illustrates how the frequency 610 of the RFID signal 381 decreases from a first frequency 631 at the first time 621 (e.g., before or at the start of the dose setting operation) to a second frequency 632 at the second time 622 (e.g., after or at the end of the dose setting operation). In some instances, the value of the second frequency 631 corresponds to the amount of the dose set by the drug delivery device 100. In some instances, the value of the difference between the first frequency 631 and the second frequency corresponds to the amount of the dose set by the dose setting mechanism of the drug delivery device 100. Generally, the external device 390 need not measure the entire history of the frequency 610 across the dose setting operation, but only measure the frequency at either the second time 622 or at the first and second times 621, 622, as detailed above. While FIG. 6 illustrates the change in frequency 610 with respect to time 602 as linear during a dose setting operation, other relationships are possible, if not more likely due to the typical non-constant movement of the dose dial sleeve 230 during a dose setting operation. In many instances, the shape of the curve of the frequency 610 does not matter, as any measured value of the frequency can, some instances, correspond directly a position 319 of the dose dial sleeve 230 (e.g., an amount of medicament set by the user), and there need not be a 1:1 correspondence such that an equal change in frequency 610 corresponds to an equal change in position 319.

Figure 7:
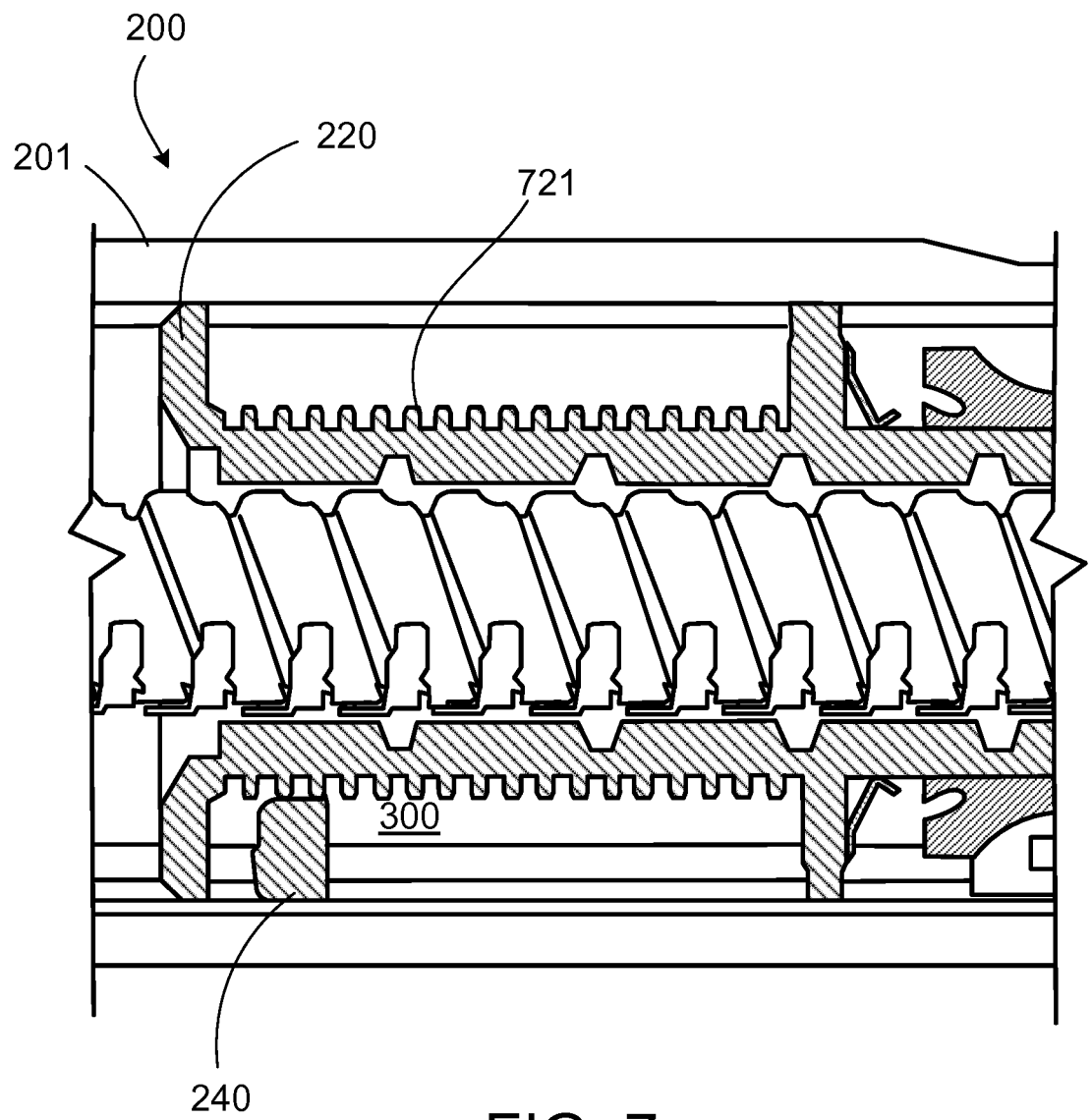
FIG. 7 is an illustration of a dose memory mechanism with a conductive track forming a variable electronic device of a dose tracking mechanism.

FIG. 7 is an illustration of a dose memory mechanism including a last dose nut 240 traveling along a conductive track 721 of the drive sleeve 220, which together form a variable electronic component of an RFID device 300. The conductive track 721 includes parallel conductive elements that sit on each side of the tread in the drive sleeve 220 and is closed at one end. The last dose nut 240 includes an RFID device 300 with two contacts that each connect to one of the two conductive elements in the conductive track 721, thereby putting the conductive track 721 in an electric circuit with the RFID device 300. The length of the conductive track 721 that is included in the RFID device 300 varies with the position of the last dose nut 240, and the position of the last dose nut 240 varies in the same way that the resistance changes in the RFID device 300. In some instances and as shown in FIG. 1, the last dose nut 240 is a half-ring nut providing enough space for a miniaturized passive RFID-chip. In operation, the last dose nut 240 is advanced along the conductive track 721 during a dose dispensing operation to a position proportional to the dose of medicament remaining in the drug delivery device 100.

Figure 8:
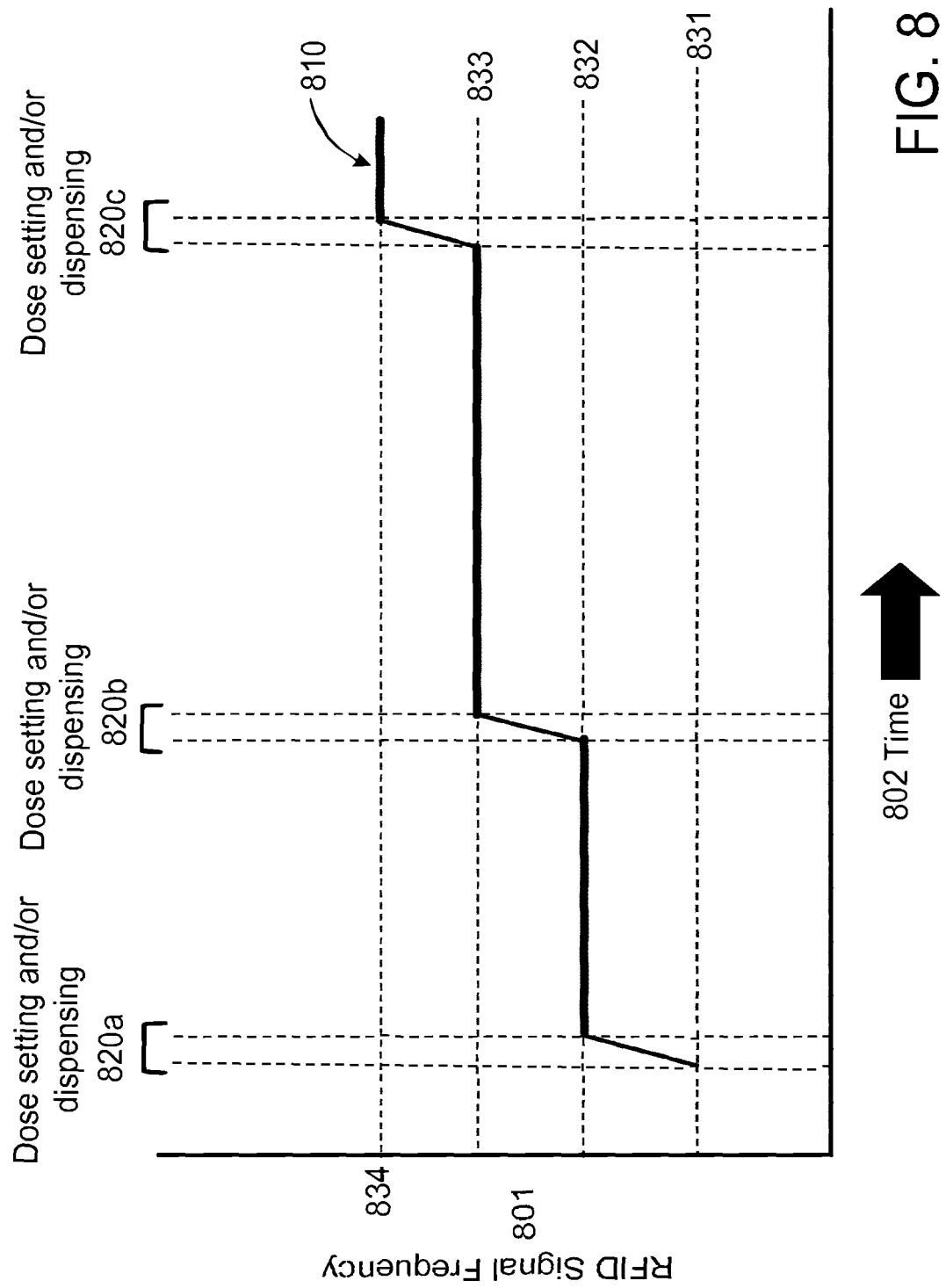
FIG. 8 is a graph of a change in the resonance frequency of an RFID device coupled to a dose memory mechanism during multiple dose dispensing operations.

FIG. 8 is a graph of a change in the resonance frequency of an RFID device 300 coupled to a dose memory mechanism during multiple dose dispensing operations. FIG. 8 illustrates how such that frequency 810 of the RFID signal 381 increases from an initial frequency 831 to a first frequency 832 during a first dose dispensing operation 820a, and then to a second frequency 833 during a second dose dispensing operation 820b, and finally to a third frequency 834 during a third dose dispensing operation. In some instances, the value of the initial frequency 831 corresponds to the position of the last dose nut 240 in the drug delivery device 100 before any use (e.g., as packaged during manufacture). This initial position of the last dose nut 240 corresponds to an initial amount of the medicament in the drug delivery device 100, Therefore, the value of the first frequency 832 corresponds to an amount of medicament remaining in the drug delivery device 100 after a first dose dispensing operation 820. Similarly, the second and third frequencies 833, 834 correspond to an amount of medicament remaining in the drug delivery device 100 after second and third dose dispensing operations 820b, 820c, respectively. Generally, the external device 390 need not measure the entire history of the frequency 810 across the dose dispensing operations, but only measure the frequency at either some time before or after each dose dispensing operation 820a-c, as detailed above.

Aspects of the systems disclose above enable medical injectors to employ 'smart' technologies by way of an attached of the included electronic components (e.g. RFID, sensor) to give a certain features to a cartridge of a drug delivery device (e.g. of a pen-type injector). When integrating electronics into drug delivery device, a one or more components may be active (e.g., a sensor to measure certain properties of the injector or cartridge) and require an energy source, which typically could be a battery. One alternative is to use a means of energy harvesting as a power source replacement for a battery.

While the above descriptions refer to two conductive elements spanning a single track (e.g., track 531 of FIG. 5A) or two conductive elements spanning individual tracks (e.g., tracks 211, 213 of FIG. 2A), one skilled in the art will appreciate that single track configurations other configurations are suitable for constructing a variable electronics device. For example, in FIG. 7, the conductive track 721 may include a single conductive element, which is contacted by the last dose nut 240. In a single-track embodiment, the RFID device 300 needs to be connected to both the last dose nut 240 (e.g., a moving location) and one end of the conductive track 721 (e.g., a stationary location). Therefore, an advantage of the track having two conductive elements connected together at one end of the track is that an RFID deice 300 need only be connected to either to both conductive elements at (i) a single location on the moving component (e.g., on the last dose nut 740 where the RFID device 300 bridges the two conductive elements) or (ii) a single location along the track (e.g., at the end of the track 721, where the last dose nut 740 bridges the conductive elements). In both cases, the position of the last dose nut 740 determines the overall length of the conductive elements in a circuit with the RFID device 300.

Embodiments of the present disclosure can also apply to prefilled single and double chamber syringes that may not use a cartridge. In some instances, the dose tracking mechanism is contained in the cartridge or in the drug delivery device in a manner enabling the dose tracking mechanism assembly to sense a change in the fill level of the cartridge or syringe after an injection. In some instances, components of the electronics assembly are located outside of the cartridge or in different parts of the cartridge or drug delivery device.

Some of the features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described embodiments by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba); B29-N—(N-lithocholyl-gamma-glutamyl)-des(B30) human insulin; B29-N-(o-carboxyheptadecanoyl)-des(B30) human insulin and B29-N-(o-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope of the present disclosure, which encompass such modifications and any and all equivalents thereof.

A number of embodiments of the present disclosure have been described. Nevertheless, it will be understood that various modifications may be made without departing from the spirit and scope of the present disclosure. Accordingly, other embodiments are within the scope of the following claims.

What is claimed is:

1. A dose tracking mechanism for use in a drug delivery device, the dose tracking mechanism comprising:
   a housing;
   a moveable component configured to move with respect to the housing during operation of the drug delivery device; and
   an RFID device comprising:
      an electric circuit having a resonance frequency, the electric circuit comprising:

an antenna configured to transmit a wireless RFID signal at the resonance frequency, and an electrical component operatively coupled to the moveable component and configured to modify the resonance frequency based on a position of the moveable component, such that the resonance frequency of the electric circuit is an indication of the position of the moveable component, wherein the moveable component is configured to vary an electrical property of the electrical component as a function of the position of the moveable component, wherein the resonance frequency of the RFID device is a function of the electrical property, wherein the electrical property is one or more of the following: capacitance, inductance, or resistance, and wherein the resonance frequency is an indication of at least one of: a set dose of medicament, a dispensed dose of medicament, or a total dose of medicament remaining in the drug delivery device.

2. The dose tracking mechanism of claim 1, wherein the moveable component is configured to move between a plurality of positions with respect to the housing, and wherein each of the plurality of positions of the moveable component causes a different resonance frequency of the electric circuit of the RFID device, such that each different resonance frequency is an indication of a different position of the moveable component.

3. The dose tracking mechanism of claim 1, comprising a dose setting mechanism having the moveable component, and wherein the position of the moveable component corresponds to the set dose of medicament to be delivered by the drug delivery device as set by the dose setting mechanism, and wherein the resonance frequency is an indication of the set dose of medicament set doseby the dose setting mechanism.

4. The dose tracking mechanism of claim 1, comprising a dose dispensing mechanism having the moveable component, and wherein a position of the moveable component corresponds to the dispensed dose of medicament dispensed from the drug delivery device by the dose dispensing mechanism, and wherein the resonance frequency is an indication of the dispensed dose of medicament dispensed from the drug delivery device.

5. The dose tracking mechanism of claim 1, comprising a dose memory mechanism having the moveable component, and wherein the position of the moveable component corresponds to the total dose of medicament remaining in the drug delivery device, and wherein the resonance frequency is an indication of the total dose of medicament remaining in the drug delivery device.

6. The dose tracking mechanism of claim 1, wherein the electrical component is a variable resistor comprising a conductor disposed in a track along the moveable component.

7. The dose tracking mechanism of claim 6, wherein the track is a first track comprising a first conductor, and the variable resistor comprises a second conductor disposed in a second track along the moveable component.

8. The dose tracking mechanism of claim 1, wherein the electrical component is a variable resistor comprising:
a first component comprising:
a track spanning at least a portion of a length of the first component, and
first and second conductors along the track; and
a second component moveable with respect to the first component along the track, the second component contacting the first and second conductors to form an electrically closed path; and wherein the electrically closed path has a resistance proportional to a position of the second component along the length of the first component, wherein the electric circuit of the RFID device is connected to the variable resistor, wherein the moveable component of the drug delivery device comprises the first component or the second component, and wherein the position of the second component with respect to the first component is changed during a dose setting operation or a dose dispending operation of the drug delivery device.

9. The dose tracking mechanism of claim 8, wherein the track comprises a single thread and the first and second conductors are disposed on opposite sides of a crest of the single thread, and wherein the second component is in threaded engagement with the first component.

10. The dose tracking mechanism of claim 8, wherein the track comprises a first thread and a second thread, and the first conductor is disposed along the first thread, and the second conductor is disposed along the second thread, and wherein the second component is in threaded engagement with the first component.

11. The dose tracking mechanism of claim 8, wherein the first component is a threaded sleeve configured to move helically with respect to the housing during the dose setting operation, and wherein the second component is a thread insert carried by the housing, wherein the moveable component is the threaded sleeve and the resonance frequency corresponds to a dose set during the dose setting operation.

12. The dose tracking mechanism of claim 8, wherein the first component is a leadscrew configured to move helically with respect to the housing during the dose dispensing operation of the drug delivery device to translate a stopper into a cartridge of the drug delivery device, wherein the second component comprises a bearing nut carried by the housing, and wherein the moveable component is the leadscrew and the resonance frequency corresponds to the position of the stopper in the cartridge which corresponds to a dose dispensed from the cartridge during the dose dispensing operation.

13. The dose tracking mechanism of claim 8, wherein the first component is a threaded plunger rod, and the second component is a last dose nut configured to thread along a drive sleeve during the dose setting operation, and wherein the moveable component is the last dose nut and the resonance frequency corresponds to a dose remaining in the drug delivery device.

14. The dose tracking mechanism of claim 1, wherein the wireless RFID signal comprises identification information related to the drug delivery device or a medicament contained therein.

15. The dose tracking mechanism of claim 1, wherein the RFID device is a passive RFID device configured to transmit the wireless RFID signal in response to a wireless reader signal received by the electric circuit of the passive RFID device.

16. The dose tracking mechanism of claim 1, wherein the RFID device comprises a power source, and wherein the RFID device is an active RFID device configured to receive power from the power source and to transmit the wireless RFID signal using the received power.

17. The dose tracking mechanism of claim 16, wherein the active RFID device is configured to transmit the wireless RFID signal in response to an activation of a trigger mechanism of the drug delivery device, the trigger mechanism initiating a dose dispensing operation.

18. The dose tracking mechanism of claim 17, wherein the RFID device is configured to transmit a first wireless RFID signal before the dose dispensing operation and a second wireless RFID signal after the dose dispensing operation.

19. The dose tracking mechanism of claim 18, wherein a resonance frequency of the first wireless RFID signal corresponds to a dose set by a dose setting mechanism or a dose remaining in the drug delivery device before the dose dispensing operation, and a resonance frequency of the second wireless RFID signal corresponds to the dose dispensed during the dose dispensing operation or the total dose remaining in the drug delivery device after the dose dispensing operation.

* * * * *